United States Patent [19]
Griffiths et al.

[11] Patent Number: 5,616,822
[45] Date of Patent: Apr. 1, 1997

[54] CALIBRATION SYSTEMS

[75] Inventors: Richard F. Griffiths, Altrincham; John Lawrence, Clwyd.; Aled Williams, Llanfairfechan, all of United Kingdom

[73] Assignee: The Secretary of State for Defence in Her Britannic Majesty's Government of the United Kingdom of Great Britain and Northern Ireland, a British Corporation Sole, London, England

[21] Appl. No.: 433,406

[22] PCT Filed: Nov. 12, 1993

[86] PCT No.: PCT/GB93/02334
§ 371 Date: Jun. 8, 1995
§ 102(e) Date: Jun. 8, 1995

[87] PCT Pub. No.: WO94/11732
PCT Pub. Date: May 26, 1994

[30] Foreign Application Priority Data

Nov. 19, 1992 [GB] United Kingdom ............... 9224304

[51] Int. Cl.⁶ .................................................. G01N 31/00
[52] U.S. Cl. ........................................................ 73/1.06
[58] Field of Search ................................................ 73/1 G

[56] References Cited

U.S. PATENT DOCUMENTS

| | | | |
|---|---|---|---|
| 3,290,920 | 12/1966 | Novak | 73/1 G |
| 3,776,023 | 12/1973 | Budd et al. | 73/1 G |
| 3,920,396 | 11/1975 | Schuy . | |
| 4,254,797 | 3/1981 | Mayeaux | 73/1 G |
| 4,544,369 | 10/1985 | Skakoon et al. . | |
| 4,656,865 | 4/1987 | Callan | 73/1 G |
| 4,931,041 | 6/1990 | Faeser . | |
| 4,970,891 | 11/1990 | Blevins et al. | 73/19.01 |

*Primary Examiner*—Robert Raevis
*Attorney, Agent, or Firm*—Nixon & Vanderhye P.C.

[57] ABSTRACT

A calibration system includes an air system having a blower unit (10), a flow meter (16) and means (15) for controlling an airflow through a mixing manifold (17) to which a metered amount of a test gas can be added from either a mass flow controller (19) or a syringe drive unit (21).

11 Claims, 5 Drawing Sheets

CALIBRATION SYSTEMS

BACKGROUND OF THE INVENTION

1. Field of the Invention

The present invention relates to systems providing an accurately variable known concentration of one gas in a mainstream of another gas, and is particularly concerned with such systems for use in calibrating instruments such as gas detection devices. The mainstream will usually be air and will, for convenience, be referred to hereafter as an airstream.

2. Discussion of the Prior Art

Gas detection devices which provide a measure of tracer or pollutant gas (henceforth, for convenience, referred to as test gas) in an airstream are well known. Devices which operate on the principle of ionisation of the test gas by means of ultra-violet light are described in, for example, GB 1576474 and WO 93/12354. In the devices described in these documents an airstream containing test gas is subjected to ultra-violet light and is passed between a pair of electrodes. Ionisation of the test gas results in the flow of electrical current between the electrodes and measurement of this current can, with calibration of the devices, provide an indication of the concentration of the test gas in the airstream.

The conventional method of calibration relies on commercially provided supplies of bottled gases containing requisite ratios of calibration gases in an undetectable carrier/buffer. This method has many disadvantages, amongst which are;

economy, in that successful calibration requires a large number of different mixtures, and in that each separate mixture is seldom completely used: in fact each calibration usually only requires only very small quantities of each mixture, and at relatively infrequent intervals, practicality, in that detection devices of the type referred to require calibration on site, which requires a disproportionate effort to be devoted to the transport and manipulation of calibration equipment and mixtures, and technical validity, in that the calibration gases are supplied as nominal mixtures, which require Further costly assay to confirm their precise composition. Furthermore the carrier gas itself may be contaminated. It is also preferable that the actual test gases which will be used or met in the field should be used in the calibrations rather than commercial equivalents.

U.S. Pat. No. 4,094,187 describes a stack gas analyzing system with a built in calibrating capability. Samples of stack gas are collected by a stack probe and passed to a series of gas analyzers, there being a separate analyzer for each possible contaminant gas. Sources, one for each suspected contaminant gas, provide supplies of contaminant gases which can be diluted by atmospheric air and fed to the gas analyzers either through the stack probe or directly. Concentrations of contaminant gases in the calibration flow are established by means of a flowmeter directly downstream of each gas supply and a flowmeter downstream of the air/contaminant gas mixing point. Delivery of calibration gas supplies must be carried out at pressures which cause displacement of stack gas from the analyzers.

The instruments described in GB1576474 and WO 93/12354 are field instruments which by reason of their function must be portable. This makes the inclusion of a built-in calibration means such as that described in U.S. Pat. No. 4,094,187 impracticable.

SUMMARY OF THE INVENTION

The present invention provides an apparatus which overcomes these disadvantages.

According to the present invention a calibration apparatus having a mixing manifold, means for connecting the manifold to a device to be calibrated, and means for supplying air from the ambient air to the manifold, is characterised in that it includes;

means for metering the supply of air to the manifold;

two alternative delivery systems, a first delivery system containing a plurality of comparatively low capacity syringes ganged together (i.e., arranged to act together) to a first common driving means and a second delivery system containing a plurality of comparatively high capacity syringes ganged together to a second common driving means, each syringe being individually connectable to, or disconnectable from, the mixing manifold, by connection means, and means for supplying a test gas to the syringes.

The means for supplying air might comprise an air filter, a blower unit and a flow meter, and the air supply might be controlled by a variable capacity blower or by use of an air bleed valve.

The connection means might be a solenoid valve, which might also be used to connect its associated syringe to the test gas supply means.

In one form of the invention the first delivery system contains four syringes having capacities respectively of 10 ml, 10 ml, 250 μl and 2.5 ml and the second delivery system has two syringes having capacities of 100 ml.

The calibration apparatus is preferably portable.

BRIEF DESCRIPTION OF THE DRAWINGS

Some embodiments of the invention will now be described, by way of example only, with reference to the accompanying diagrammatic drawings, of which.

DETAILED DISCUSSION OF PREFERRED EMBODIMENT

Figure 1:
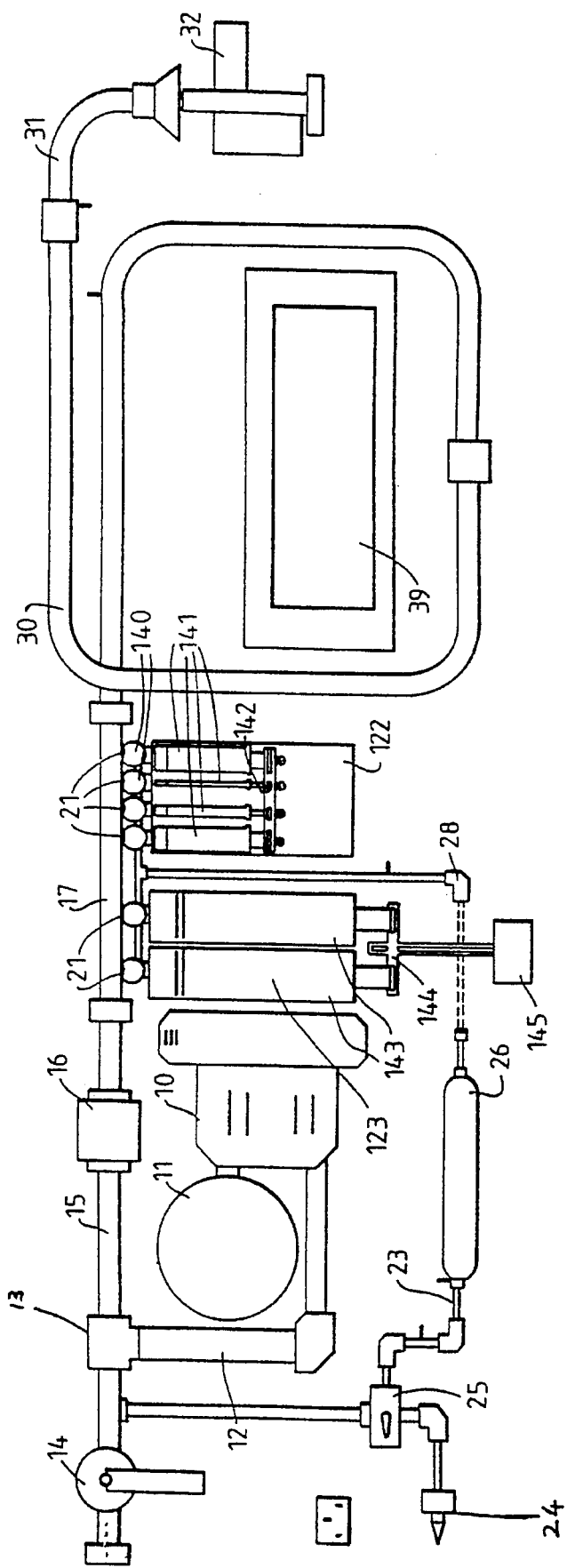
FIG. 1 shows the mechanical layout of a test system according to the invention.

A calibration system (FIG. 1) has a blower 10 connected to an ambient air supply by a filter 11. The blower 10 is connected by tubing 12 to a T junction 13 from which a first leg leads to an air bleed valve 14 and a second leg leads via a flow straightener 15 to a turbine flow meter 16. The turbine meter 16 is connected to a mixing manifold 17 which inputs 21 from syringes 141, 143.

A test gas supply line 23 connectable to a test gas supply 24 has an inlet valve 25 and an expansion chamber 26, and has a connection 28 to solenoid valves 140, one For each syringe 141, 143. Each solenoid valve can be switched to connect its associated syringe to the test gas supply 28 or to the manifold 17.

The syringes are arranged into first and second delivery systems 122, 123. The first delivery system 122 has four small capacity syringes 141 ganged together by a ganging member 142 and are driveable by a stepping motor (not shown). Typical capacities for these might be 10 ml for two, 250 µl for a third and 2.5 ml for a fourth. The second delivery system 123 has two large capacity syringes 143 ganged together by a ganging member 144 and are driveable by a stepping motor 145. A typical capacity for each syringe might be 100 ml.

The mixing manifold 17 is connected by a mixing tube 30 to a diffuser 31 to which can be attached a device 32 to be calibrated.

Figure 2:
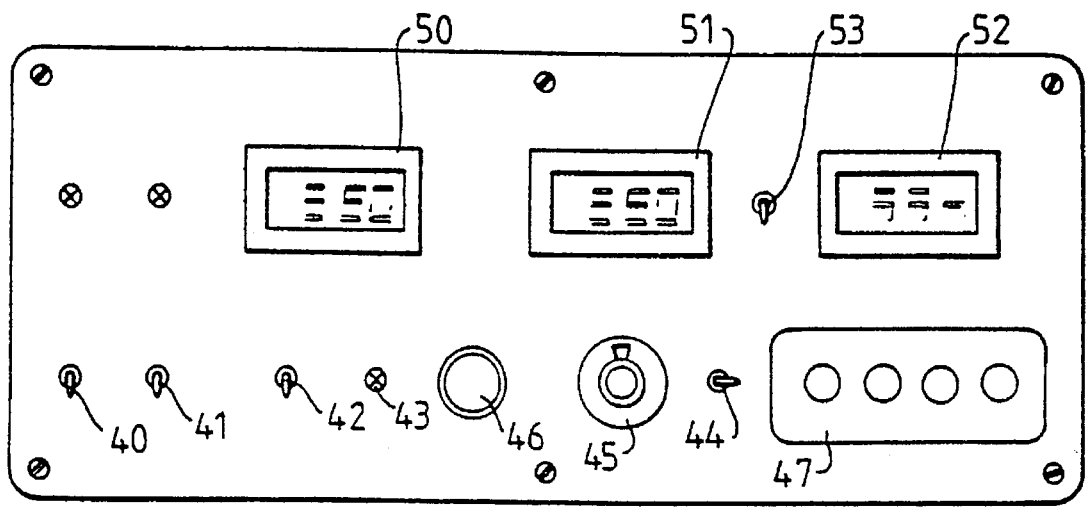
FIG. 2 shows the Front panel controls of the system.

A system control unit has a control panel 39 on which are positioned (FIG. 2) a power supply switch 40, a blower switch 41, a flow switch 42 by which either a high or a low blower flow can be selected, a low flow indicator 43 which gives an indication if the airflow drops below a predetermined minimum, a selector switch 44 which allows either the first delivery system 122 or the second delivery system 123 robe connected to the mixing manifold 17, a control switch 45 by which the output of the second delivery system 123 can be adjusted, a selector switch 46 which allows selection of one or both syringes 143 of the second delivery system 123, and a syringe keyboard 47 to Control selection of the syringes 141 of the first delivery system 122. Also on the control panel are an air supply gauge 50, a mass flow controller supply gauge 51, a syringe programme indicator 52 and a purge switch 53.

Figure 3:
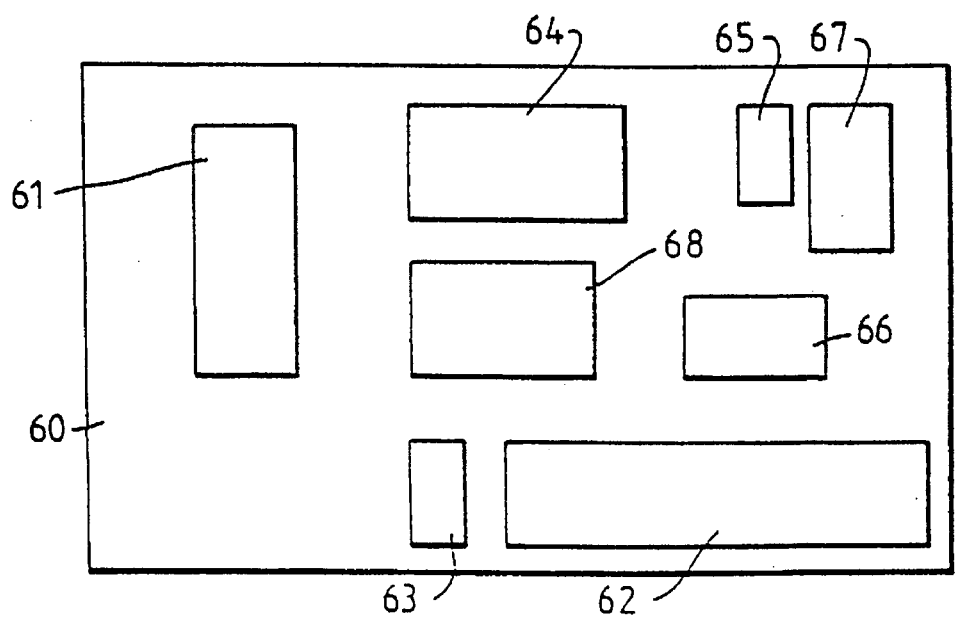
FIG. 3 shows the electronic chassis layout of the system.

An electronics chassis 60 (FIG. 3) has mounted thereon electronic systems relating to the syringe unit 61, syringe drive and display board 62, solenoid drive board 63, flow meter unit 64, input connector block 65, front panel connector board 66, power supply 67 and miscellaneous systems 68.

Figure 4:
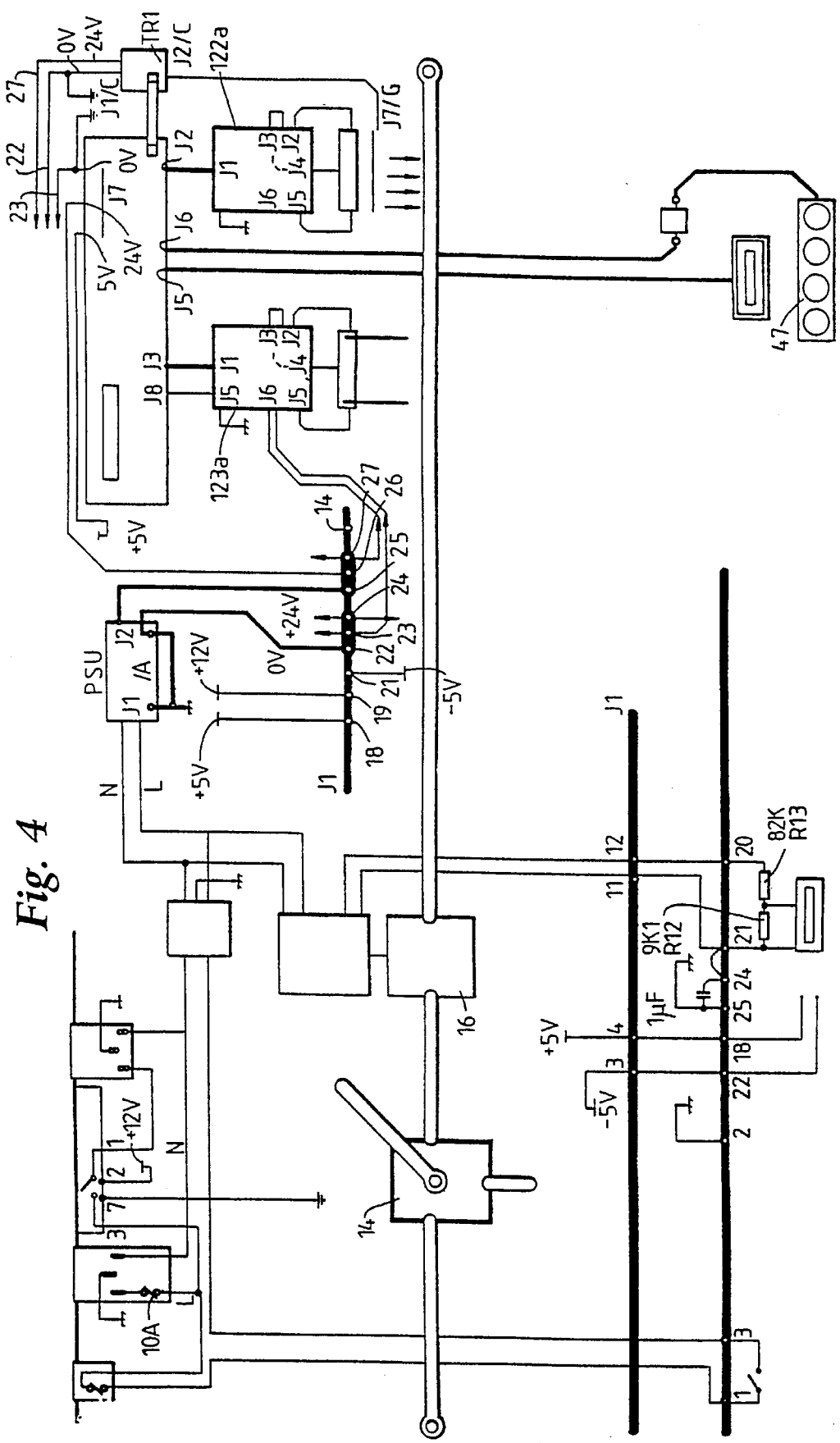
FIG. 4 shows the control block diagram.

The control block diagram is shown in FIG. 4, where items relating to items described with reference to FIG. 1 are identified by numerals as used for the items. In particular, the control block includes a first delivery system controller 122a and a second delivery system controller 123a.

Figure 5:
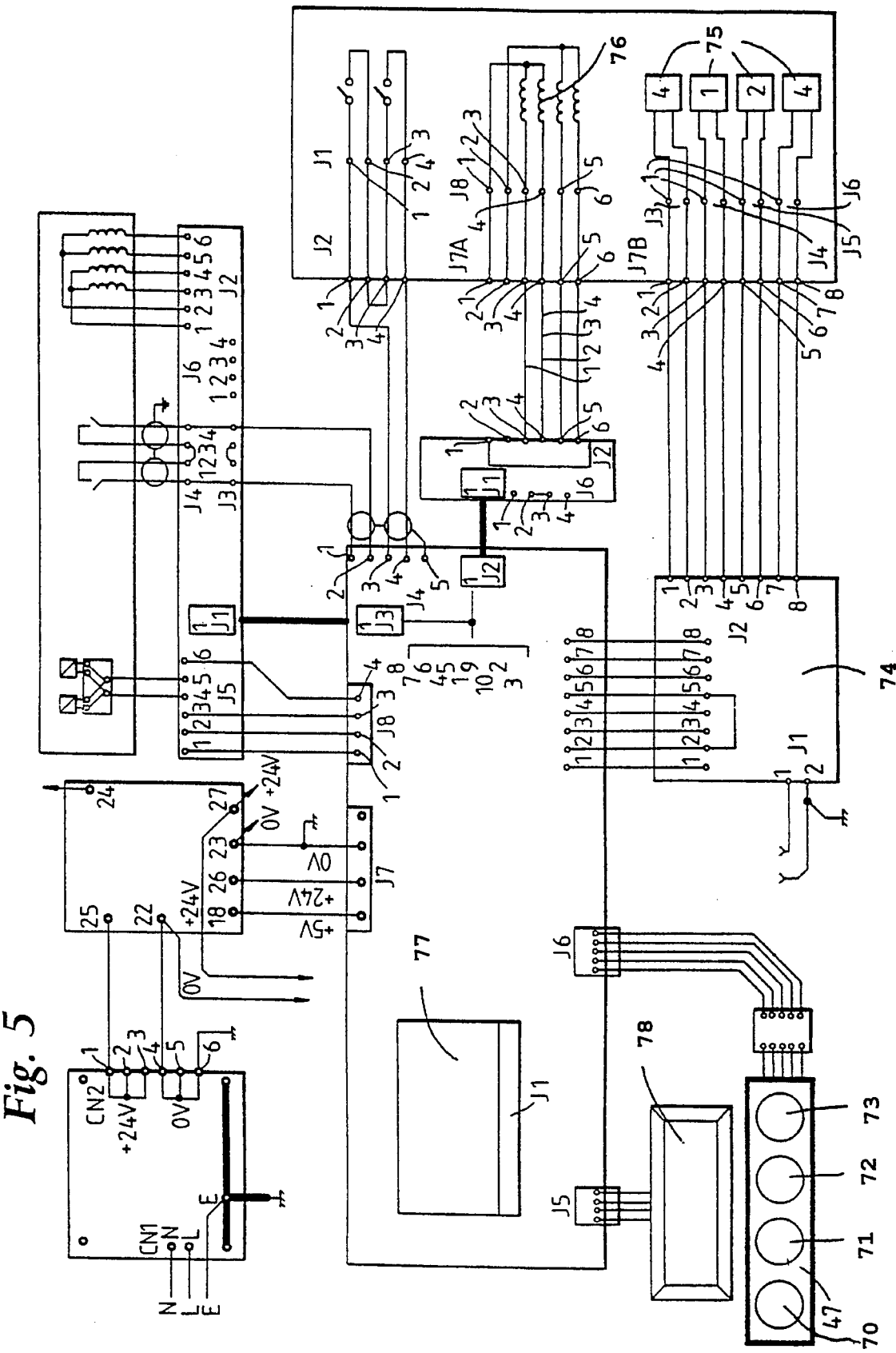
FIG. 5 shows connections to a syringe unit used in the system.
Figure 6:
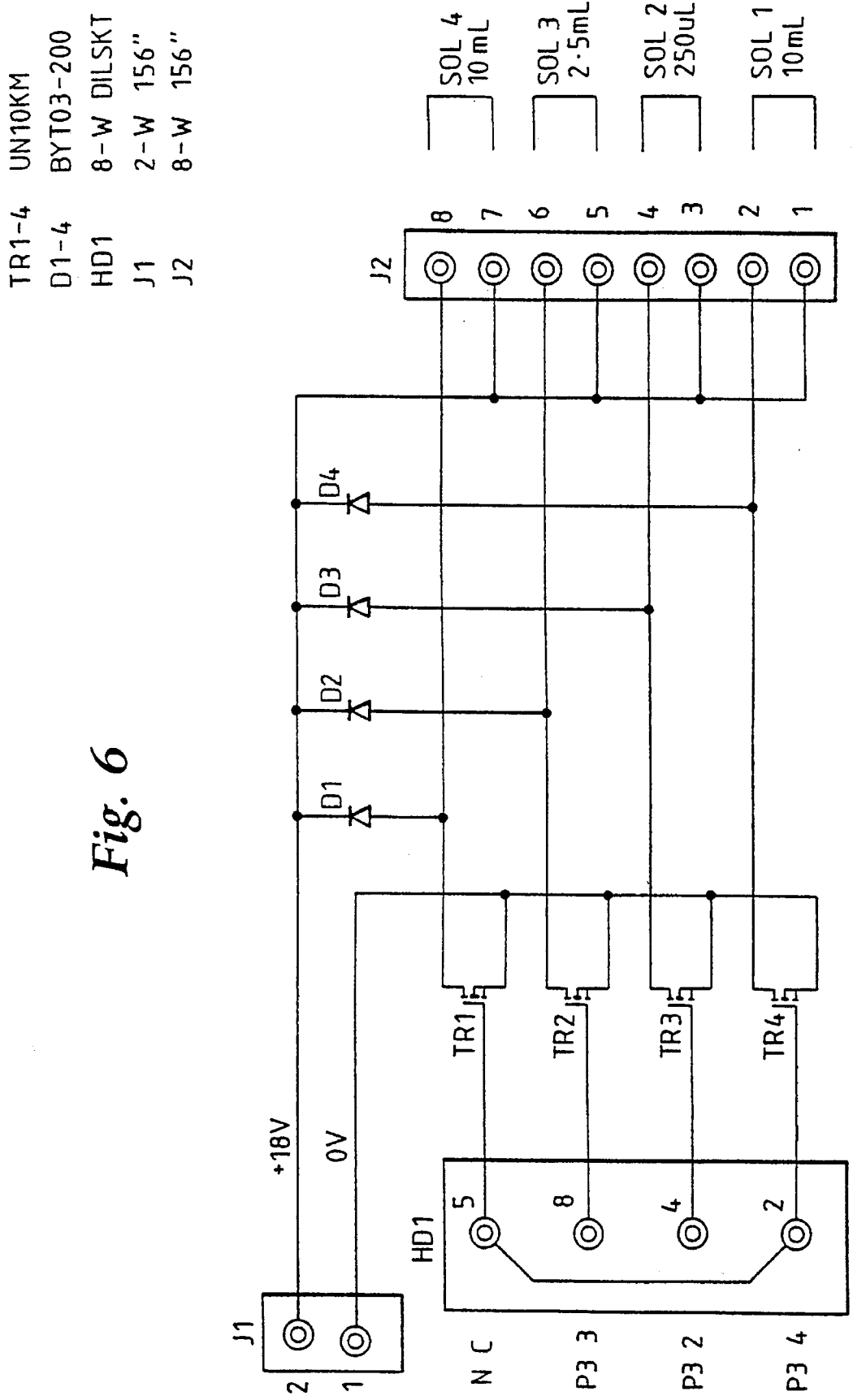
FIG. 6 shows connections to a solenoid driver used for driving the syringe unit.

A syringe control unit for the first delivery system 122 (FIG. 5) includes the keyboard 47 by which the syringe 141 output can be adjusted by means of a primary function (start/stop) St key 70, < key 71, a > key 72 and a Function Fn key 73. This unit also contains a solenoid driver 74 (see also FIG. 6) solenoid valves 75, a stepping motor 76 for driving the syringes 141. LCD displays 77, 78 and various other equipment.

Examples of components suitable for use in the invention are a a Quadrina Flow Meter QBG/16B/EP1, a GAST Reginair Blower R1102, a RS Power Supply 594-763, and Hamilton Syringes.

The system is prepared for a calibration by connecting a test gas container 24 to the supply line 23 and a unit 32 to be tested to the diffuser 31. The test gas system is then purged by blowing test gas therethrough, with the blower 10 operating to prevent test gas from flowing back towards the blower, and by operating the syringes 141, 143.

The syringes 141, 143 are then connected to the test gas supply 28 by appropriate operation of the solenoid valves 140 and are filled with test gas, which is allowed to stabilise to atmospheric pressure.

The system is programmed to provide a sequence of concentrations of test gas in the airflow, using test gas from the syringes 141, 143 of the first and second delivery systems 122, 123 as appropriate. Calibration is then carried out by running the sequences through the item 32. Results are plotted manually or automatically on recording instruments in the usual way. During the calibration syringes 141, 143 are connected by the solenoid valves 140 to the mixing manifold 17 the stepping motors driven at appropriate speeds, syringes 141, 143 not required for a particular calibration point being connected to the test gas input 28 so that gas therefrom flows back along the system, excessive build up of pressure being prevented by the presence of the expansion, chamber 26.

It will be realised that many alternative arrangements and components are possible within the scope of the invention, and that exact operating procedures will depend on these. For example, drive motors other than stepping motors might be used for driving the syringes 141, 143, or an individual drive motor might be provided for some or all of the syringes. In some circumstances it might be acceptable to vent gas to atmosphere from syringes rather than returning it to the system. The syringes may be installed in mope than the two units described. Also alternative delivery systems might be used to replace those described above. Many alternative types of flowmeter might be used.

What is claimed is:

1. A calibration apparatus comprising:

a mixing manifold (17), means (30) for connecting the manifold to a device (32) to be calibrated, means (14, 15) for supplying air from the ambient air to the manifold (17), means (16) for metering the supply of air to the manifold (17);

two alternative delivery systems (122, 123), a first delivery system (122) containing a plurality of comparatively low capacity syringes (141) ganged together (142) to a first common driving means (76) and a second delivery system (123) containing a plurality of comparatively high capacity syringes (143) ganged together (144) to a second common driving means (145), each syringe (141, 143) being individually connectable to, and disconnectable from the mixing manifold (17) by connection means (140), and means (23, 24, 28) for supplying a test gas to the syringes (141, 143).

2. A calibration apparatus as claimed in claim 1 wherein the means for supplying air comprises an air filter (11), a blower unit (10) and a flow meter (16).

3. A calibration apparatus as claimed in claim 2 wherein said blower unit includes a variable capacity blower (10).

4. A calibration apparatus as claimed in claim 2 wherein the air supply is controlled by the use of an air bleed valve (14).

5. A calibration apparatus as claimed in claim 1 wherein the connection means (140) comprises a solenoid valve.

6. A calibration apparatus as claimed in claim 5 wherein the solenoid valve (140) is used to connect its associated syringe (141, 143) to the test gas supply means (23, 24, 25).

7. A calibration means as claimed in claim 1 wherein the first delivery system (122) contains four syringes (141).

8. A calibration apparatus as claimed in claim 7 wherein the (141) syringes have capacities respectively of 10 ml, 10 ml, 250 µl and 2.5 ml.

9. A calibration apparatus as claimed in claim 1 wherein the second delivery system (123) has two syringes (143).

10. A calibration apparatus as claimed in claim 9 wherein the syringes (143) have capacities of 100 ml.

11. A calibration apparatus as claimed in claim 1 wherein said apparatus is portable.

\* \* \* \* \*